United States Patent [19]

Boltze et al.

[11] 4,332,727
[45] Jun. 1, 1982

[54] PREPARATION OF 1-(4-CHLOROBENZOYL)-5-METHOXY-2-METHYL-3-INDOLYLACETOXYACETIC ACID

[75] Inventors: Karl-Heinz Boltze, Bergisch-Gladbach; Siegfried Raddatz; Peter-Rudolf Seidel, both of Cologne, all of Fed. Rep. of Germany

[73] Assignee: Troponwerke GmbH & Co. KG, Cologne, Fed. Rep. of Germany

[21] Appl. No.: 193,497

[22] Filed: Oct. 2, 1980

[30] Foreign Application Priority Data

Oct. 25, 1979 [DE] Fed. Rep. of Germany ....... 2943125

[51] Int. Cl.$^3$ ............................................ C07D 209/28
[52] U.S. Cl. ........................... 548/501; 260/326.14 R; 564/251
[58] Field of Search ............. 260/326.14 R, 326.14 A

[56] References Cited

U.S. PATENT DOCUMENTS 3,910,952 10/1975 Boltze et al. ............... 260/326.13 A
3,962,471 6/1976 Bieve et al. ................ 260/326.12 A

FOREIGN PATENT DOCUMENTS 43-19949 8/1968 Japan .............................. 260/326.16
7041382-R 12/1970 Japan ......................... 260/326.13 A

OTHER PUBLICATIONS

Rodd, Chem. of Carbon Cmpds., vol. IV, part A, pp. 71–73, Elsevier, N.Y., N.Y., (1957).

*Primary Examiner*—Donald G. Daus
*Assistant Examiner*—D. B. Springer
*Attorney, Agent, or Firm*—Sprung, Horn, Kramer & Woods

[57] ABSTRACT

The invention relates to a process for the production of 1-(4-chlorobenzoyl)-5-methoxy-2-methyl-3-indolylacetoxyacetic acid (known to be useful as an antiphlogistic agent) which comprises reacting α-(4-chlorobenzoyl)-4-methoxyphenylhydrazine hydrochloride or sulphonate with laevulinoyloxyacetic acid and cyclizing the resulting hydrazone to obtain a product free from 1-benzoyl-5-methoxy-2-methyl-3-indolylacetoxyacetic acid.

2 Claims, No Drawings

PREPARATION OF 1-(4-CHLOROBENZOYL)-5-METHOXY-2-METHYL-3-INDOLYLACETOXYACETIC ACID

The present invention relates to an unobvious and advantageous process for the production of particularly pure 1-(4-chlorobenzoyl)-5-methoxy-2-methyl-3-indolylacetoxyacetic acid, which is known.

A number of processes have already been disclosed for the preparation of this known compound (see DT-OS (German Published Specification) No. 2,234,651 corresponding to GB Pat. No. 1,411,350 and DT-OS No. 2,257,867 corresponding to U.S. Pat. No. 4,104,278).

In all these processes, the carboxyl group is first protected by a benzyl radical, so that catalytic hydrogenation of the benzyl ester according to the following equation has to be carried out in a last reaction step.

Equation:

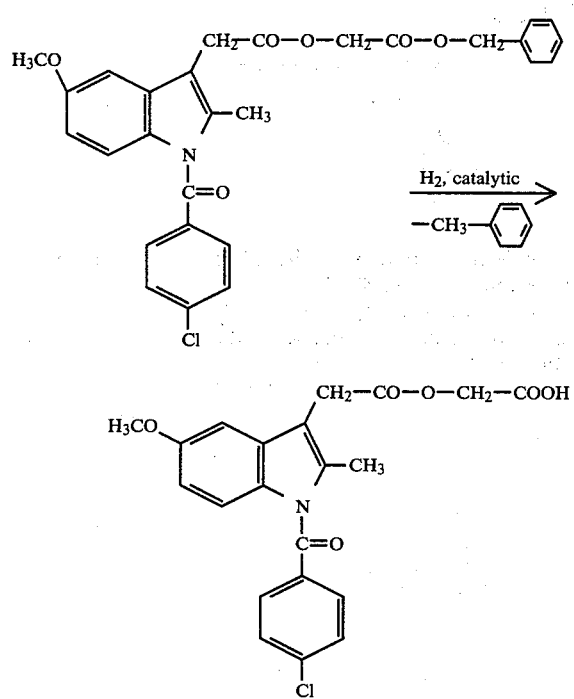

1-Benzoyl-5-methoxy-2-methyl-3-indolylacetoxyacetic acid (the de-chloro compound) is always formed as a by-product during this splitting off of the benzyl radical. This undesired impurity, which is formed in an amount of up to 0.5% by splitting off the chlorine from the benzene ring of the 4-chlorobenzoyl radical, must then subsequently be removed in expensive purification steps, this removal being associated with losses in yield.

The present invention provides an alternative preparation process which allows the formation of the undesired de-chloro compound to be avoided.

According to the present invention there is provided a process for the production of 1-(4-chlorobenzoyl)-5-methoxy-2-methyl-3-indolylacetoxyacetic acid in which α-(4-chlorobenzoyl)-4-methoxyphenylhydrazine hydrochloride of the formula

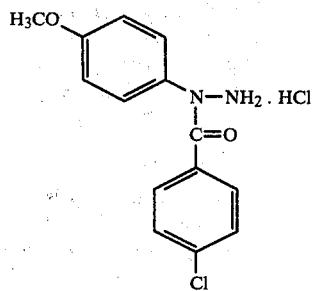

or the corresponding sulphonate, is reacted with free laevulinoyloxyacetic acid of the formula $$CH_3\text{-}CO\text{-}CH_2\text{-}CH_2\text{-}COO\text{-}CH_2\text{-}COOH \qquad (II)$$

in glacial acetic acid as the solvent, at a temperature between 20° and 60° C., and the hydrazone initially formed, of the formula

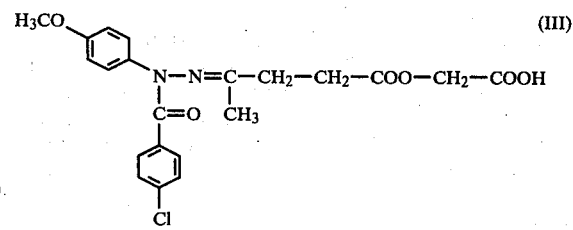

is cyclized to the desired indole, ammonia being split off, by heating to 40° to 80° C., the cyclisation to the indole optionally being carried out under an inert gas atmosphere. The process of the present invention surprisingly allows 1-(4-chlorobenzoyl)-5-methoxy-2-methyl-3-indolylacetoxyacetic acid to be obtained in a simple manner and in high purity.

It could not have been expected that 1-(4-chlorobenzoyl)-5-methoxy-2-methyl-3-indolylacetoxyacetic acid would be formed in such pure form, that is to say free from the troublesome de-chloro compound, and in yields of 60 to 70% of theory by this process.

The hydrazine compound of the formula (I) employed in carrying out the process according to the invention is known (see British Pat. No. 1,148,909).

Laevulinoyloxyacetic acid of the formula (II) was not known hitherto, but it can be prepared in a simple manner, by subjecting laevulinoyloxyacetic acid benzyl ester, which is known (literature: Tatsuo Yamanaka and Heinosuke Yasuda, Scientific Research Institute Ltd., Japan 272 ('58), January 23rd cited in C.A. 53, 1157e and DT-OS No. 2,234,651 corresponding to GB-Pat. No. 1,411,350) to catalytic hydrogenation.

The end compound prepared by the process according to the invention is a valuable pharmaceutical active compound with an antiphlogistic action (see German Patent Specification No. 2,234,651 corresponding to GB Pat. No. 1,411,350).

The following Examples illustrate the process of the present invention.

EXAMPLE 1

0.6 to 0.8 mol of laevulinoyloxyacetic acid is dissolved in 600 to 800 ml of glacial acetic acid, and 0.4 mol of α-(4-chlorobenzoyl)-4-methoxyphenylhydrazine hydrochloride is added at 50° C. The mixture is allowed to react at 50° to 70° C. under a nitrogen atmosphere for 2 hours. After addition of 750 ml of water, and after seeding with a few crystals of 1-(4-chlorobenzoyl)-5-methoxy-2-methyl-3-indolylacetoxyacetic acid, the product precipitates in yellow crystals of melting point 151° to 152° C. Yield: 65% of theory.

EXAMPLE 2

0.36 mol of laevulinoyloxyacetic acid is dissolved in 350 ml of glacial acetic acid, and 0.24 mol of finely ground α-(4-chlorobenzoyl)-4-methoxyphenylhydrazine hydrochloride is added at 50° C.

The mixture is stirred at 55° to 57° C. under nitrogen for 1 hour, the temperature is then increased by 5° C. and the mixture is allowed to react for a further hour. 265 ml of water are added to the hot batch and crystallisation is started by seeding with a few crystals. A further 175 ml of water are added in the course of 30 minutes, whilst stirring, until the temperature reaches 20° C. The mixture is subsequently stirred for a further 60 minutes and the product which has precipitated is then filtered off. It is washed with 100 ml of 30% strength acetic acid and 500 ml of water and a colourless, crystalline product is obtained. The crude yield of this water-containing product is 90% of theory. The water content is determined as 20%, so that this crude product contains 70% of theory of the end product. The crude product is dried at 90° C. under a waterpump vacuum for 1 hour. Yellowish crystals which have a melting point of 151° to 152° C. are obtained.

Yield: 63% of theory.

What is claimed is:

1. A process for the production of 1-(4-chlorobenzoyl)-5-methoxy-2-methyl-3-indolylacetoxyacetic acid, substantially free from 1-benzoyl-5-methoxy-2-methyl-3-indolylacetoxyacetic acid, which comprises the step of reacting α-(4-chlorobenzoyl)-4-methoxyphenylhydrazine hydrochloride of the formula

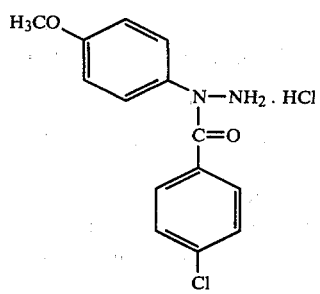

or the corresponding sulphonate, with free laevulinoyloxyacetic acid of the formula

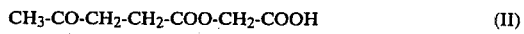

in glacial acetic acid as the solvent, at a temperature between 20° and 60° C., and cyclizing the hydrazone initially formed, of the formula

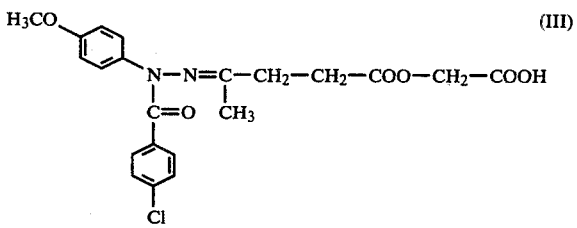

to the desired indole, with the splitting off of ammonia by heating to 40° to 80° C.

2. A process according to claim 1, in which the cyclization to the indole is carried out under an inert gas atmosphere.

* * * * *